(12) United States Patent
Aberg

(10) Patent No.: US 7,390,816 B2
(45) Date of Patent: Jun. 24, 2008

(54) METHODS FOR TREATING URINARY INCONTINENCE IN PATIENTS SUFFERING FROM MEMORY DISORDERS

(75) Inventor: A.K. Gunnar Aberg, Sarasota, FL (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

(21) Appl. No.: 11/453,698

(22) Filed: Jun. 15, 2006

(65) Prior Publication Data

US 2006/0293356 A1 Dec. 28, 2006

Related U.S. Application Data

(60) Provisional application No. 60/692,470, filed on Jun. 21, 2005.

(51) Int. Cl.
*A61K 31/44* (2006.01)
(52) U.S. Cl. ..................................................... 514/278
(58) Field of Classification Search ........................ None
See application file for complete search history.

(56) References Cited

U.S. PATENT DOCUMENTS

| | | | |
|---|---|---|---|
| 3,480,626 A | 11/1969 | Pfleger et al. ............ | 260/247.2 |
| 5,112,872 A | 5/1992 | Baba et al. .................... | 514/73 |
| 5,998,430 A | 12/1999 | Schwantes et al. .......... | 514/299 |
| 6,207,852 B1 * | 3/2001 | Aberg et al. .................. | 560/57 |
| 6,482,837 B1 | 11/2002 | Wood .......................... | 514/315 |
| 6,974,820 B2 | 12/2005 | Aberg ......................... | 514/278 |
| 2002/0010216 A1 | 1/2002 | Rogosky et al. ............. | 514/649 |
| 2003/0144352 A1 | 7/2003 | Cammarata et al. ......... | 514/531 |

FOREIGN PATENT DOCUMENTS

WO 98/00390 1/1998

OTHER PUBLICATIONS

Kay et al., "Antimuscarinic Agents: Implications and Concerns in the Management of Overactive Bladder in the Elderly", Clinical Therapeutics, vol. 27 No. 1, (Jan. 2005), pp. 127-138.*
Scheife et al., "Central Nervous System Safety of Anticholinergic Drugs for the Treatment of Overactive Bladder in the Elderly", Clinical Therapeutics, vol. 27, No. 2, (Feb. 2005), pp. 144-153.*
Ulshofer, et al., Clin. Drug Invest. 2001: 21(8): 563-569; "Randomised, Double-Blind, Placebo-Controlled Study on the Efficacy and Tolerance of Trospium Chloride in Patients with Motor Urge Incontinence".
Pharmacology & Toxicology 1999, 85, 299-304: Svane Beckmann-Knopp et al.; "Inhibitory Effects of Trospium Chloride on Cytochrome P450 Enzymes in Human Liver Microsomes".
Bertholdt H. et al., Arzneimittel-Forsch, 17; 719-726, no date available.
Biochemical Pharmacology, vol. 22, pp. 3099-3108. Pergamon Press, 1973; Yung-Chi Cheng et al.,; "Relationship Between the Inhibition Constant (K1) and the Concentration of Inhibitor which causes 50 per cent Inhibition (I50) of an Enzymatic Reaction".
The Lancet; vol. 338; Aug. 10, 1991 pp. 344-345; M.J. Connolly et al.; "Torsades de pointed ventricular tachycardia and terodiline".
Chrysalis; P.A. Gayheart-Walsten, et al..; "Effects of a New Non-Sedating Antihistamine on Qtc Interval in a Newly developed Guinea Pig Model", no date available.
Journal of Cardiovascular Pharmacology; 37: 607-618; 2001; Gary A. Gintant et al.; "The Canine Purkinje Fiber: An In Vitro Model System for Acquired Long QT Syndrome and Drug-Induced Arryhythmogenesis".
Dig. Dis 1992: 10: 38-45; Juha M. Gronroos et al.; "Cholinergic Hypothesis of Alcoholic Pancreatitis".
Clinical Pharmacology & Therapeutics Jul. 1996; 07019901; pp. 89-98; Kenneth Hartigan-Go, MD et al.; "Stereoselective Cardiotoxic Effects of Terodiline".
Abstracts 487-488; 85A; Hofner et al.; "Tolerability and Efficacy of Trospium Chloride in a Long-Term Treatment (52 weeks) in Patients with urge-Syndrome: A Double-Blind, Controlled, Multicentre Clinical Trial", no date available.
Ital Heart J. Suppl. 2000; 1 (3): 419-422; Imperadore et al.; "Arresto cardiaco da fibrillazione ventricolare in corso do pancreatitte acuta biliare: descrizone di un caso clinico e ipotesi eziopatogentiche".
Page from Medscape from WEBMD; Rhythm disorders in gallstones; no date provided http://intapp.medscape.com/ps/medlineapp/getdoc.org=1&searchid=15& have-local-holdings-file=1&local-journal-only=O &searchstring=%22arrhythmia%22+and+%22cholelithiasis%22.
British Journal of Pharmacology (2000) 131, 245-254; Stephen E. Jones et al.; "Differences in the effects of urinary incontinence agents S-oxybutynin and terodiline on cardiac K+ currents and action potentials".
The Journal of Pharmacology and Experimental Therapeutics; vol. 247, No. 3; pp. 867-872; James F. Kachur et al.; "R and S Enantiomers of Oxybutynin: Pharmacological Effects in Guinea Pig Bladder and Intestine", no date provided.
Pharmacology & Toxicology 1998, 82, 161-166; Eeva Lukkari et al.; "Cytochrome P450 Specificy of Metabolism and Interactions of Oxybutynin in Human Liver Microsomes".
British Journal of Urology (1995), 75, 452-456; H. Madersbacher et al.; "Trospium Chloride Versus Oxybutynin: a randomized double-blind, multicentre trial in the treatment of detrusor hyper-reflexia".
The Journal of Urology; vol. 148, 595-597, Aug. 1992; Charlotte A. Massad et al.,; "The Pharmacokinetics of Intravesical and Oral Oxybutynin Chloride".
The Journal of Pharmacology and Experimental Therapeutics; vol. 256, No. 2; L.Noronha-Blob et al.; "Enantiomers of Oxybutynin: In Vitro Pharmacological Characterization at M1, M2 and M3 Muscarinic Receptors and in Vivo Effects on Urinary Bladder Contraction, Mydriasis and Salivary Secretion in Guinea Pigs", No date provided.

(Continued)

*Primary Examiner*—Raymond J. Henley, III
(74) *Attorney, Agent, or Firm*—Nields & Lemack

(57) ABSTRACT

Methods are disclosed using trospium, an antimuscarinic smooth muscle relaxant, for the treatment of smooth muscle disorders, while avoiding the concomitant liability of adverse side effects associated with conventional antimuscarinic treatment.

19 Claims, No Drawings

OTHER PUBLICATIONS

Eur J Clin Pharmacol (1994) 47: 337-343; A.Pietzko et al.; "Influences of trospium chloride and oxybutynin on quantitative EEG in healthy volunteers".

Drug Metabolism and Disposition vol. 26, No. 4 pp. 289-293; Hans Postlind et al.; "Tolterodine, A New Muscarinic Receptor Antagonist, Is Metabolized by Cytochromes P450 2D6 and 3A in Human Liver Microsomes", no date provided.

The Journal of Pharmacology and Experimental Therapeutics; vol. 290, No. 3; pp. 1417-1426; Shuba et al.; "Action Potentials, Contraction, and Membrane Currents in Guinea Pigs Ventricular Preparations Treated with the Antispasmodic Agent Terodiline", no date provided.

Arzneimittel-Forschung/Drug Research 48 (11), 10, 1012-1018 (1998); Smith et al. "Comparison of the Antimuscarinic and Antispasmodic Actions of Racemic Oxybutynin and Desethyloxbutynin and Their Enantiomers with Those of Racemic Terodiline".

Page from Medscape from WEB MD; "Effects of Tolterdoine, Trospium Chloride, and oxybutynin on the central nervous system", no date provided, http://intapp.medscape.com/px/medlineapp/getdoc?ord=4&searchid=3&have-local-holdings-file=1&local-journals-only=0&searchstring=trospium.

Clin Drug Invest 23(6); 395-404, 2003; diefenback et al.; "Randomised, Double-Blind Study of the Effects of oxybutynin, Tolterodine, Trospium Chloride and Placebo on Sleep in Healthy Young Volunteers".

Dmochowski *Urology, Supplement 6A, 56, 2000, p. 41-49).

Kuhn et al. (Z Kardiol, Dec. 1976, 65(12), 1071-87, Abstract).

Schladitz-Keil et al. (Arzneimittelforschung, Jun. 1986, 36(6), 984-7), Abstract.

Goodman & Gilman's: The Pharmacological Basis of Therapeutics (2001), Tenth Edition, Chapter 19, pp. 448-449.

The Merck Manual of Diagnosis and Therapy: Sixteenth Edition (1992) pp. 1403-1404.

Torres, C.A., et al. Acad. Emerg. Med 2006, 13, S187.

* cited by examiner

METHODS FOR TREATING URINARY INCONTINENCE IN PATIENTS SUFFERING FROM MEMORY DISORDERS

This application claims priority of Provisional Application Ser. No. 60/692,470 filed Jun. 21, 2005, and called Methods For Treating Smooth Muscle Contractions Using Trospium, the disclosure of which is hereby incorporated in its entirety by reference.

FIELD OF THE INVENTION

This invention relates to a compound named trospium, the chloride salt thereof having the formula:

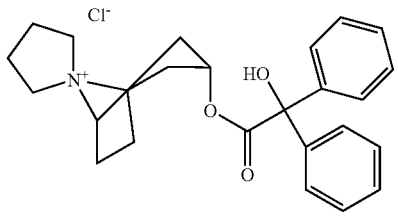

Trospium Chloride

The generic name Trospium Chloride (CAS-10405-02-4; INN) refers to an anticholinergic compound with the chemical name azoniaspiro (3☐-benziloyl-oxynortro-pane-8,1'-pyrrolidine) chloride; $C_{25}H_{30}ClNO_3$; MW=427.97.

Trospium can be synthesized as described by Pfleger R. et al. in U.S. Pat. No. 3,480,626 and by Bertholdt H. et al., Arzneimittel-Forsch, 1967, 17: 719-726.

Trospium Chloride may be purchased from Galen Ltd, Craigavon, UK or from Madaus A G, Köln, Germany. Trospium can also be extracted from 20 mg trospium tablets (Regurin®, Madaus in Germany or Sanctura®, Indevus in USA), using extraction methods commonly known to those skilled in the art.

The compound trospium has several known metabolites, the most well known being the spiroalcohol. The spiroalcohol metabolite has antimuscarinic activities that are believed to contribute to the therapeutic activity of Trospium Chloride.

The present invention relates specifically to the therapeutic use of trospium, possible prodrugs thereof and the active metabolites of trospium and the possible prodrugs thereof, and pharmaceutical compositions containing at least one of said compounds for treating smooth muscle hyperactivity disorders, such as for example urinary disorders, including urinary incontinence and pollakiuria, and gastrointestinal disorders, including gastrointestinal hyperactivity, and other smooth muscle hyperactivity or hyperreactivity disorders including those occurring in conjunction with asthma, bronchitis, urolithiasis, cholelithiasis and choledocholithiasis, while avoiding certain serious recognition (memory) side effects, said side effects on memory being considered to be hallmarks of antimuscarinic medication.

The risk for severe memory side effects of antimuscarinic medication is particularly high in patients with pre-existing memory disorders or in patients at risk for developing memory disorders or in patients already using other medication that may have effects on cognition, such as for example oxybutynin (Ditropan®, Alza) and diphenhydramine (Benadryl®, Pfizer), or in elderly patients. In this document, the term "elderly" refers to individuals at the age of 65 years and older.

BACKGROUND OF THE INVENTION

Trospium has been shown to reduce bladder hyperactivity in patients suffering from urinary incontinence and exerts spasmolytic effects on the bladder by inhibiting the effects of acetylcholine on smooth muscle. Thus, Trospium Chloride is an anticholinergic drug. Trospium Chloride has selectivity for muscarinic receptors over nicotinic receptors and as a result, no blocking effects are observed at skeletal neuromuscular junctions. Thus, the anticholinergic drug Trospium Chloride can also be called an antimuscarinic drug. Active metabolites of Trospium Chloride exert antimuscarinic activities that are believed to account for part of the therapeutic activity of trospium.

The terms 'anticholinergic' and 'antimuscarinic' are interchangeable in this document.

The terms 'Memory Disorders' and 'memory disorders' are interchangeable in this document.

The terms "predisposed" (to memory disorder) and "propensity" (for developing memory disorders), which are interchangeably used herein, refer to individuals who are at risk for developing Memory Disorders.

The term "urge incontinence" is in this document includes "over-active bladder" (OAB) and includes the disease called pollakiuria (frequent urinations).

Individuals who are predisposed to memory disorder may suffer from intermittent or "on and off" expression of memory disorders. After being diagnosed, memory disorders may also be intermittent, or appear "on-and-off" in patients; thus patients suffering from memory disorders may have symptoms that alternate between more or less severe.

Memory is the ability of the brain to retain and recall information.

Anti-cholinergic drugs are known to cause impairment of memory (Katz I. R., et al., J Am Geriatr Soc 1998, 46: 8-13). The leading drugs for Alzheimer's disease are cholinergic drugs, such as cholinesterase inhibitors, which have the opposite effect of common anticholinergic drugs, such as for example oxybutynin. Examples of cholinergic drugs that are used to improve memory functions are tacrine, (Cognex®, Pfizer); galantamine, (Reminyl®, Janssen); revastigmine, (Exelon®, Novartis) and donepezil, (Aricept®, Pfizer). Furthermore, withdrawal of anticholinergic medication usually causes immediate improvement of memory (Mori K., et al. Pharmacopsychiatry 2002, 35: 6-11).

Memory disorders can be of different types, such as Mild Impairment of Memory (including for examples forgetfulness and difficulty in remembering names), Amnesia (memory disorder affecting recollection of recent events), and Dementia (memory disorders affecting recollection of both recent and distant events). Alzheimer's Disease (AD) and Vascular Dementia (VaD) are the two leading causes of dementia in the elderly, with AD being the most prevalent type). A common type of memory disorders in the elderly is Senile Dementia, with various sub-forms, such as for example pre-senile dementia, which can be diagnosed in individuals that most often are of the age 65 years or older. In the case of pre-senile dementia, the disorder is often diagnosed in patients younger than 65 years of age. Thus, memory impairment can be a symptom of any of the aforementioned memory disorders.

While local concentrations of acetylcholine in the basalis magnocellularis of the forebrain are important for cognition, the physiological/anatomical basis for recollection (memory) is far less obvious. It is also very likely that short-term memory functions are different from long-term memory functions. Thus AD patients often have vivid long-term memory, but severe lack of short-term memory. It is obvious to those skilled in the art that cholinergic mechanisms are involved in memory functions, although it cannot of course be excluded that other neurotransmitters in the brain may also be involved. Basic and clinical studies have revealed that memory dysfunction in patients suffering from Alzheimer's disease is correlated with low concentrations of acetylcholine in the brain.

Memory disorders are usually diagnosed when a patient complains of memory loss. While a sophisticated diagnosis is usually made by a specialist, general practitioners often rely on specific diagnostic criteria. Physicians have also found The Mini-Mental State Examination (MMSE) to be useful for the diagnosis of certain forms of memory disorders, such as for example dementia. (Santacruz K. S., Swagerty D.: Early diagnosis of Dementia. Am Fam Physician 2001; 63: 703-713). The MMSE shall only be performed by qualified medical personnel, and the test can be purchased by physicians from PAR Customer Support, 16204 N. Florida Avenue, Lutz, Fla. 33549. However, patients suffering from Mild Memory Impairment often perform like normal elderly persons and when given the MMSE, their score is usually 24 or higher, but they perform worse than normal individuals when tested for verbal and spatial memory (Brandt J. Am Fam Physician 2001, Vol. 63: Number 4, Editorial).

Test exist that can be used instead of the MMSE or in conjuncture with the MMSE. Furthermore, experienced physicians may be able to diagnose memory disorders without the help of a standardized test.

It is a method of the present invention to determine if patients, who are suffering from smooth muscle disorders, are simultaneously suffering from or having a propensity for developing memory disorders and if said determination is positive, administering to said patients a therapeutically effective amount of trospium or an active metabolite thereof or a pharmaceutically acceptable salt or solvate thereof. Said determinations can be performed by a physician using interviews, physical examination and/or application of a standardized test, such as for example the Mini-Mental State Examination (MMSE). While it is fairly easy to determine if a patient suffers from a memory disorder, it can be more difficult to determine if a patient is predisposed for the development of a memory disorder. While the ultimate ability to make this diagnose depends on the experience of the physician, age is most often considered to be a risk factor for the development of memory disorders. Other risk factors are for example cerebral atherosclerosis, untreated hypertension, alcohol or illegal drug abuse. It is possible that hereditary factors can be involved.

It is well known to those skilled in the art of psychiatric health care that anticholinergic drugs have a worsening effect on memory function in patients suffering from memory disorders and said types of drugs may induce memory disorders in patients who are predisposed to memory disorders or in patients who are at an early stage in the development of a memory disorder.

To have a direct effect on certain areas of the brain, drugs have to cross the blood-brain barrier (BBB). This barrier is made up of layers of cells, surrounding the small blood vessels that supply the brain with oxygen and nutrition. The BBB was previously believed to be a simple mechanical barrier, keeping all large molecules and all charged molecule out of the brain. Thus, factors believed to influence the ability of drugs to cross the blood-brain barrier were believed to include ionization (pKa), lipophilicity (log P) and molecular weight (MW). However, the knowledge about the nature of the BBB, its functions and its limitations have improved tremendously and it is now known that the BBB is not simply a mechanical barrier, but also has mechanisms in place for the active transport of molecules out of the brain. The BBB can become "leaky" (more permeable) of numerous reasons, such as for example by influence from the hormone epinephrine that is known to cause leakage of the BBB, thereby making it possible for various molecules to pass through the BBB and enter into the brain. Diseases, such as cognitive disorders, type-II diabetes and hypertension are often correlated with increased permeability of the EBB. It is also known that certain drugs can induce increased permeability of the BBB. Examples of such drugs are certain angiotensin converting enzyme inhibitors and phenylephrine. It is also well-known that the blood-brain barrier deteriorates with age (Toornvliet J R, et al. J Cerebral Blood Flow & Metabolism, 2005, 25: 273; Bronge L, et. al. Dement Geriatr Cogn Disord, 2000, 11:263-267.) This is of importance in connection with the pharmacology of drugs for geriatric diseases like urinary urge incontinence, which almost exclusively affect the elderly. Acute studies on blood-brain barrier in healthy young volunteers (with healthy and well functioning BBB) are of no or very limited relevance to the elderly patients who are suffering from various chronic disorders, such as for example urinary urge incontinence (Todorova A, B, J Clin Pharmacol. 2001; 41:636-644). In general, quaternary amines penetrate the healthy BBB less readily than tertiary amines, however, quaternary amines are known to cross the BBB, even in healthy individuals. Thus, as a well-known example, the quaternary choline esterase inhibitor pyridostigmine was able to penetrate the BBB in American soldiers, causing the Persian Gulf Syndrome (PGS) in gulf war soldiers (Haley et al. JAMA, 1977, 277: 223-230.) Numerous other quaternary cholinergic drugs are known to cross the BBB and cause CNS-related side effects, such as for example the quaternary drugs edrophonium that causes convulsions and restlessness and neostigmine that causes dizziness, convulsions, drowsiness and headache and hyoscine (Buscolysin®, Sopharma) that has side effects such as anxiety and hallucinations.

Furthermore, the BBB is absent from significant parts of the brain, such as for example the hypothalamus, the pituitary and pineal areas, area postrema and areas of the choroids plexus.

It can be assumed that quaternary compounds, such as trospium will be able to cross the blood-brain barrier rather slowly in healthy and young individuals, but in elderly individuals and particularly in elderly patients with existing diseases, quaternary compounds have the ability to cross the blood-brain barrier. The reason why trospium does not have negative effects on memory and why trospium does not aggravate existing memory disorders is unknown.

To our knowledge, no known reference teaches or enables the methods of the present invention comprising administering trospium to a human suffering from Memory Disorders or being at risk for developing Memory Disorders; nor do the published references alone or in combination suggest these methods. It is of importance to note that many patients in earlier stages of Memory Disorders, express memory malfunctions that have a tendency to be intermittent or "come and go". Elderly patients are considered to be at increased risk for developing memory disorders of various types.

SUMMARY OF THE INVENTION

Pharmacological studies of Trospium Chloride have now been performed in comparison with known and marketed antimuscarinic drugs with therapeutic activity against cholinergically mediated diseases, such as for example urinary incontinence.

Thus, present studies have confirmed that trospium, as well as darifenacin, tolterodine and oxybutynin, have potent antimuscarinic activity.

It has also been found that while antimuscarinic drugs for incontinence, such as for example oxybutynin can cause memory side effects, trospium, surprisingly, does not cause this side effect, even under circumstances where the permeability of the blood-brain barrier has experimentally been increased. Thus, trospium can safely be used as a treatment for urinary urge incontinence and other smooth muscle disorders while not aggravating memory disorders, in patients suffering from such disorders or in patients being predisposed for memory disorders, which is contrary to other anticholinergic medications that are used to treat said smooth muscle diseases.

The ability to memorize is characteristic for humans and other species, but the biological mechanisms of memory are not well understood. However, it is known that memories are stored in the brain through strengthening of the synapses between neurons and it is known that neurons must turn on the synthesis of new proteins for synaptic strengthening and long-term memory to occur. It is also known by those skilled in the art that there is an activation signal from the synapse that is activating the protein synthesis and an enzyme called "mitogen-activated protein kinase" (MAPK) provides a molecular switch that triggers long-term memory storage by activating protein synthesis mechanisms. Furthermore, a growth-associated protein, called GAP-43, is found in neurons and in no other organs of the body, GAP-43 has to be in a phosphorylated form in order to initiate the formation of memory-holding proteins in the neurons. The mechanisms for formation and retention of memories seem to be well preserved among animal species and there are striking similarities between memory-retention in animals and man. There are, however, still many unknown mechanisms that regulate both the formation and the retention of the protein-induced strengthening of the neuronal synapses and it is an interesting fact that most anti-cholinergic drugs, largely through unknown mechanisms, cause memory impairment, while compounds that increase the concentration of acetylcholine in the brain have the opposite effect, as is obvious from the fact that memory-enhancing drugs for Alzheimer patients increase the concentration of acetylcholine in the brain. It is not known how cholinergic drugs are involved in the retention of memories and it is commonly observed that forgotten memories can reappear when anti-cholinergic therapy is interrupted. Given this background, it is surprising that the potent anti-muscarinic drug trospium does not cause memory impairment, which is contrary to other antimuscarinic drugs. Thus, as examples, it is not known if this is due to unknown or less known cerebral muscarinic receptors on the neurons or if there are other mechanisms involved that protect the neuronal synapses from the effects of trospium.

Since trospium has now been found not to express said type of memory impairment as expected from antimuscarinic drugs, such as for example oxybutynin, in laboratory animals, it is concluded that trospium will offer anticholinergic treatment for muscarinic disorders, including urinary voiding disorders such as urinary urge incontinence and for gastrointestinal disorders, including gastric motility disorders such as diarrhea in humans, while avoiding the concomitant liabilities of adverse side effects on memory that are usually associated with antimuscarinic drugs. Trospium will therefore offer potential for anticholinergic treatment for smooth muscle disorders, including urinary incontinence and gastrointestinal smooth muscle disorders including increased activity or hyperactivity of said gastrointestinal smooth muscle and kidney and gall bladder disorders, such as urolithiasis and cholelithiasis and choledocholithiasis, while not causing worsening of memory disorders of patients suffering from such disorders and while not causing memory disorders in patients at risk for developing such disorders and in patients with early symptoms of memory disorders, said symptoms of memory disorders being known by those skilled in the art as "stop-and-go" or intermittent symptoms of memory disorders.

In cases where urgent anti-muscarinic treatment is preferred, trospium can be administered parenterally, such as by the intravenous route to rapidly alleviate smooth muscle spasm and the pain in connection with urolithiasis or cholelithiasis or choledocholithiasis. Continued treatment of the patients can use oral administration of trospium.

Urinary incontinence is a disease that in many patients is not consistent, but it is recurrent and many patients take their medication to prevent the reoccurrence of the symptoms of their disease. The magnitude of a prophylactic or therapeutic dose of a compound of the present invention in the acute or chronic management of disease will vary with the severity and nature of the condition to be treated and with the route of administration. The dose and the frequency of the dosing will also vary according to the age, body weight, expected results and response of the individual patient. Doses as low as 1 mg to as high as 240 mg, as a single dose or divided into repeated doses, may be administered daily to patients in need of such therapy. More preferred are daily doses of 10 mg to 60 mg of trospium chloride, as a single daily dose or divided into repeated doses during a 24-hours period. In general, the daily oral dose of Trospium Chloride is one 20-mg tablet twice daily to patients suffering from urinary urge incontinence. In managing the patient, the therapy may be initiated at a lower dose, perhaps at about 5 mg to about 10 mg, twice daily, and is usually increased up to 20 mg depending on the patient's global response. It may be necessary to use dosages outside these ranges in some cases, as will be apparent to those skilled in the art. Further, it is noted that the clinician or treating physician will know how and when to interrupt, adjust, or terminate therapy in conjunction with individual patient response.

It is obvious for those skilled in the art that controlled-release formulation of trospium will constitute advantageous dosage forms that will not only offer convenience, but will also avoid or decrease acute antimuscarinic side effects, such as dry mouth and blurry vision, which are coupled to peak plasma concentrations of the drug.

The terms "a therapeutically effective amount" and "an amount sufficient to treat the disorder but insufficient to cause adverse effects" are encompassed by the above-described dosage amounts and dose frequency schedule.

Any suitable route of administration may be employed for providing the patient with an effective dosage of the compounds of the present invention. For example, oral, sublingual, parenteral (i.e. subcutaneous, intramuscular, intravenous, etc.), transdermal, vaginal, aerosol and like forms of administration may be employed. Additionally, the drug may be administered directly into the bladder, as described for oxybutynin by Massad C. A., et al. in J. Urol. 148, 595-597 (1992) and for Trospium Chloride by Schwantes U., et al. in U.S. Pat. No. 5,998,430 or rectally directly into the gastrointestinal canal. Dosage forms include tablets, troches, dispersions, suspensions, solutions, capsules, suppositories, microencapsulated systems, slow-release and controlled release systems, transdermal delivery systems, including, for example patches, creams, ointments and electrophoretic systems, and the like.

Prodrugs of trospium or prodrugs of the spiroalcohol metabolite can be prepared by those skilled in the art, as has been described for an active metabolite of tolterodine by Sparf B. et al. in EP 0957 073 A1, and may be administered in accordance with the present invention.

The pharmaceutical compositions of the present invention comprise of trospium or a metabolite thereof as the active ingredient, or any possible and pharmaceutically acceptable salt thereof, and may also contain a pharmaceutically acceptable carrier, and optionally, other therapeutic ingredients.

The terms "pharmaceutically acceptable salts" or "pharmaceutically acceptable salt thereof" refer to possible salts of trospium and the active metabolite of trospium. Said salts of trospium may be prepared from pharmaceutically acceptable non-toxic acids. Suitable pharmaceutically acceptable salts for the compounds of the present invention include the chloride of trospium, but also other halogen salts and salts such as acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like, if possible to synthesize and if pharmaceutically acceptable. Particularly preferred is Trospium Chloride.

The compositions of the present invention include suspensions, solutions, elixirs or solid or semi-solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations. Because of their ease of administration, tablets and capsules represent the more advantageous oral dosage unit forms, in which case solid or semi-solid pharmaceutical carriers are employed. If desired, tablets may be coated, using standard aqueous or nonaqueous techniques. Capsuls can be hard or soft.

In addition to the common dosage forms set out above, the compounds of the present invention may also be administered by controlled release means and delivery devices to obtain improved pharmacokinetic profiles (such as sustained and stable plasma levels or prolonged duration of activity) or decreased side effects. Thus, controlled-release tablet formulations of Trospium Chloride, allowing once-daily administration, have obvious advantages for the patient, as realized by those skilled in the art.

Pharmaceutical compositions of the present invention, suitable for oral administration, may be presented as discrete unit dosage forms such as capsules, cachets, suppositories, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding, in a suitable machine, a mixture of the powdered compound moistened with an inert liquid diluent. All of the foregoing techniques are well know to persons of skill in the pharmaceutical art. Each tablet or capsule may contain from about 1 mg to about 60 mg of the active ingredient. An example of an oral unit dose formulation is shown below.

EXAMPLE 1

Oral Unit Dosage Formulation (Tablets)

| Ingredients | per tablet | per batch of 10,000 tablets |
|---|---|---|
| Trospium Chloride | 20 mg | 200 g |
| Microcrystalline cellulose | 30 mg | 300 g |
| Lactose | 70 mg | 700 g |
| Calcium stearate | 2 mg | 20 g |
| FD&C Blue #1 Lake | 0.03 mg | 300 mg |

Trospium Chloride can be blended with lactose and cellulose until a uniform blend is formed. The lake can be added and further blended. Finally, the calcium stearate can be blended in, and the resulting mixture can be compressed into tablets using, for example, a 9/32 inch shallow concave punch. Tablets of other strengths may be prepared by altering the ration of active ingredient to the excipients or altering the final weight of the tablet. Slow-release or controlled-release tablets may be particularly valuable or useful.

Pharmacological Studies of Trospium

1. Ligand Binding Studies: Affinity for muscarinic receptors.

Methods:

The experiments were carried out on membranes prepared from SF9 cells that expressed human recombinant muscarinic receptor subtypes. After incubation with the test article and the proper radioligand ($^3$H scopolamine methylchloride) and washing, bound radioactivity was determined with a liquid scintillation counter, using a commercial scintillation cocktail. The specific radioligand binding to a muscarinic receptor was defined as the difference between total binding and non-specific binding determined in the presence of an excess of unlabelled atropine. $IC_{50}$ values (concentrations required to inhibit 50% of specific binding) were determined by non-linear regression analysis of the competition curves, from which affinity (pKi) values were determined (Cheng Y. et al. Biochem Pharmacol 1073, 22: 3099-3108.)

Results:

Affinity (negative logarithm of the dissociation constant Ki) of trospium and reference compounds for human recombinant receptors

|  | Test compound | | | |
| --- | --- | --- | --- | --- |
|  | M-1 | M-2 | M-3 | M-4 |
| Trospium | 9.1 | 9.2 | 9.3 | 9.0 |
| Tolterodine | 8.8 | 8.1 | 8.7 | 7.9 |
| Oxybutynin | 8.8 | 7.9 | 8.8 | 8.2 |
| Darifenacin | 8.3 | 7.7 | 9.2 | 7.4 |

Conclusions:

Trospium had slightly higher affinity for human muscarinic receptors than the reference compounds. The therapeutic activity of anti-muscarinic drugs in overactive human bladders are usually considered to be related to affinity for M-2/M-3 receptors, while the side effect xerostomia (dry mouth) is due mainly, but not exclusively, to inhibition of M-1 receptors in salivary glands.

2. Functional Characterization of Antimuscarinic and Antispasmodic

Activities on Bladder Smooth Muscle Strips.

Methods:

Experiments have now been performed using methods described by Kachur et al, J Pharmacol Exp Ther. 1988, 247: 867-872 and Noronha-Blob et al. J Pharmacol Exp Ther 256: 562-567. Strips of tissue (approximately 10 mm long and 1.5 mm wide) were removed from the urinary bladder of male guinea pigs. The tissues were suspended in an oxygenated buffer of the following composition, in mM: NaCl 133; KCl 4.7; $CaCl_2$ 2.5; $MgSO_4$ 0.6; $NaH_2PO_4$.1.3; $NaHCO_3$ 16.3; and glucose 7.7. The smooth muscle strips were maintained at or about 37.5° C. in tissue chambers and allowed to equilibrate with the bathing solution for one hour before proceeding with the experiment. Contractions induced by carbachol were used to measure anticholinergic actions of trospium and reference compounds (oxybutynin, tolterodine) as described by Smith et al., (Smith et al. 1998, 48: 1012-1018).

Results:

The antimuscarinic compounds terodiline, tolterodine, oxybutynin and trospium, potently inhibited carbachol-induced contractions with $K_B$ values between 1.5 nM and 5.5 nM. There were no differences of biological significance between these test compounds, thereby confirming results from receptor binding studies in this functional test system.

3. Side effects concerning memory functions.

Methods:

Conscious rats are used. The animals are placed at the base of a T-shaped maze with a reward placed in one of the arms of the maze. After the animals have learned where the reward is located, said reward is removed and it is investigated how long time it takes in the maze before the rats no longer selected the arm of the maze where the reward had been located. Experiments were also performed in rats that had been pretreated with phenylephrine to increase the permeability of the blood-brain barrier. Control groups of animals were treated with placebo (vehicle only) or with oxybutynin.

Results:

Results from ongoing studies demonstrate that Trospium Chloride does not influence the memory. Results from ongoing studies also demonstrate that there is no further aggravation of memory impairment when Trospium Chloride is administered to animals in which a memory disorder had been induced experimentally by treatment with oxybutynin. Pretreatment of the animals with phenylephrine did not uncover any impairment of memory by trospium.

Discussion:

The present results demonstrate that memory is impaired by administration of oxybutynin, but not by Trospium Chloride. In animals, in which impaired memory had been induced with oxybutynin, there is no further impairment or aggravation of the memory functions by the administration of trospium to the animals, even if the animals were pretreated with phenylephrine, which is a drug that is known to increase the permeability of the blood-brain barrier. It is concluded that Trospium does not have unwanted side effects on memory in this model, when given to naive animals or when given to animals that already demonstrate memory impairment. As known by those skilled in the art of pharmacology or toxicology, this animal model of memory in rodents is considered to be a relevant model for studies of effects of drugs on memory in humans.

EQUIVALENTS

Those skilled in the art will recognize, or be able to ascertain, using no more than routine experimentation, many equivalents to the specific embodiments of the invention described herein. Such equivalents include the co-administration of at least one compound of the present invention with any other drug that is used to combat diseases such as smooth muscle hyperactivity or certain conditions, such as pain, in mammals, mentioned in this document. Such equivalents also include the co-administration of at least one compound of the present invention with any other compounds or drugs that may be used for urinary incontinence, or cognition disorders. Those skilled in the art of medicine will also realize that higher or lower doses than those indicated here may be preferred and the doses may be given more or less frequently than suggested here.

Those skilled in the art, will realize that smooth muscle motility disorders, in addition to urinary bladder disorders, include disorders of the gastrointestinal tract, including gastric reflux (heart burn), diarrhea and irritable bowel syndromes (IBS) and disorders of the urinary and ducts (e.g. "kidney stone pain"; urolithiasis) and the gall fluid ducts (e.g. "gall stone pains"; cholelithiasis and choledocholithiasis) and disorders of the smooth muscles of the airways (e.g. asthma, COPD and bronchitis), which are all included in the present invention.

The term "urge incontinence" is in this document includes "over-active bladder" (OAB) and the disease called pollakiuria (frequent urinations).

Those skilled in the art of pharmacology, will realize that the compounds of the invention, being trospium and the active metabolites of trospium and possible salts and solvates thereof, having certain pharmacological properties, such as antimuscarinic activity on various receptor types, calcium antagonistic activity, spasmolytic activity on various types of smooth muscle etc., may be useful for other indications than those listed here.

The invention claimed is:

1. A method for treating chronic smooth muscle disorders in an elderly human suffering from, or having a propensity for, a memory disorder, comprising administering to said elderly human a therapeutically effective amount of trospium or a pharmaceutically acceptable salt or solvate thereof or an active metabolite of trospium or a pharmaceutically acceptable prodrug, salt or solvate thereof, while avoiding deterioration of memory functions or worsening of existing memory disorders, said deterioration of memory functions or worsening of existing memory disorders being commonly expected from antimuscarinic medication used for treating said smooth muscle disorders in elderly humans.

2. The method of claim 1, wherein said smooth muscle disorder is a voiding disorder.

3. The method of claim 2, wherein said voiding disorder is a urinary voiding disorder.

4. The method of claim 3, wherein said urinary voiding disorder is urinary urge incontinence.

5. The method of claim 1, wherein said metabolite is a spiroalcohol metabolite.

6. The method of claim 1, wherein the amount of trospium or the active metabolite thereof is administered from 1 mg to 240 mg per day.

7. The method of claim 1, wherein the amount of trospium or the active metabolite thereof is administered from 10 mg to 60 mg per day.

8. The method of claim 1, wherein the amount of trospium or a pharmaceutically acceptable salt or metabolite thereof is administered together with a pharmaceutically acceptable carrier.

9. The method of claim 1, wherein said memory disorder is a symptom of Mild Memory Impairment.

10. The method of claim 1, wherein said memory disorder is a symptom of Amnesia.

11. The method of claim 1, wherein said memory disorder is a symptom of Dementia.

12. The method of claim 1, wherein said memory disorder is a symptom of Alzheimer's disease.

13. The method of claim 1, wherein said memory disorder is a symptom of Vascular Dementia.

14. The method of claim 1, wherein said memory disorder is a symptom of Senile Dementia.

15. A method for treating smooth muscle disorders in a human, comprising determining whether said human suffers from, or has a propensity for, a memory disorder, and if said determination is positive, administering to said human in need thereof a therapeutically effective amount of trospium or an active metabolite thereof or a pharmaceutically acceptable salt thereof.

16. The method of claim 15, wherein said smooth muscle disorder is a voiding disorder.

17. The method of claim 16, wherein said voiding disorder is a urinary voiding disorder.

18. The method of claim 17, wherein said urinary voiding disorder is urinary urge incontinence.

19. The method of claim 15, wherein said propensity for a memory disorder is expressed as on-and-off manifestations of a memory disorder.

* * * * *